US007415169B2

(12) United States Patent  
Florent et al.

(10) Patent No.: US 7,415,169 B2
(45) Date of Patent: Aug. 19, 2008

(54) MEDICAL VIEWING SYSTEM AND METHOD FOR ENHANCING STRUCTURES IN NOISY IMAGES

(75) Inventors: Raoul Florent, Ville d'Avray (FR); Lucile Nosjean, Rueil-Malmaison (FR); Pierre Lelong, Nogent sur Marne (FR); Peter Maria Johannes Rongen, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 639 days.

(21) Appl. No.: 10/496,554

(22) PCT Filed: Nov. 20, 2002

(86) PCT No.: PCT/IB02/04878

§ 371 (c)(1),
(2), (4) Date: May 25, 2004

(87) PCT Pub. No.: WO03/045263

PCT Pub. Date: Jun. 5, 2003

(65) Prior Publication Data

US 2005/0002546 A1    Jan. 6, 2005

(30) Foreign Application Priority Data

Nov. 30, 2001  (EP)  ................................. 01403083
Sep. 23, 2002  (EP)  ................................. 02292336

(51) Int. Cl.
*G06K 9/32* (2006.01)
*G06K 9/40* (2006.01)
*G06K 9/36* (2006.01)
*G06K 9/00* (2006.01)

(52) U.S. Cl. ........................ 382/294; 382/266; 382/130; 382/287; 623/1.11; 606/7

(58) Field of Classification Search .................. 382/130, 382/284, 294, 287; 623/1.11; 606/7
See application file for complete search history.

(56) References Cited

U.S. PATENT DOCUMENTS 5,467,380 A * 11/1995 De Jonge et al. ........... 378/98.2

(Continued)

OTHER PUBLICATIONS

Close et al., "Improved image guidance of coronary stent deployment", Medical Imaging 2000, pp. 301-304.*

(Continued)

*Primary Examiner*—Matthew C. Bella
*Assistant Examiner*—Randolph Chu (57) ABSTRACT

A viewing system and method for enhancing objects of interest represented on a moving background in a sequence of noisy images and for displaying the sequence of enhanced images, comprising extracting means (11) for extracting features related to an object of interest in images of the sequence; registering means (12) for registering the features related to the object of interest with respect to the image referential, yielding registered images (13); similarity detection means for determining the resemblance of the representations of a registered object of interest in succeeding images and weighing means for modulating the intensities of the pixels of said object of interest over the images of the sequence; temporal integrating means (14, 33b) for integrating the object of interest and the background over a number, or at least two, registered images (13) of the sequence; and display means (54) for displaying the processed images (15, 45) of the enhanced registered object of interest on faded background. Application: Medical Imaging. X-ray Fluoroscopic Imaging.

14 Claims, 4 Drawing Sheets

U.S. PATENT DOCUMENTS

| | | | | |
|---|---|---|---|---|
| 5,982,915 A | * | 11/1999 | Doi et al. | 382/130 |
| 6,941,323 B1 | * | 9/2005 | Galperin | 707/104.1 |
| 2005/0107688 A1 | * | 5/2005 | Strommer | 600/424 |

OTHER PUBLICATIONS

Close et al. ("Layer decomposition of coronary angiograms", Image Processing, Kenneth M Hanson, Editor, Proceedings of SPIE, vol. 3979, 2000, pp. 1230-1234).*

Close R A et al: "Improved image guidance of coronary stent deployment" Medical Imaging 2000: Image Display and Visualization, San Diego, CA, USA, Feb. 13-15, 2000, vol. 3976, pp. 301-304, XP001189037.

"Layer decomposition of coronary angiograms", by Robert A. Close et alii, in Proceedings of the SPIE International Society for Optical Engineering, vol. 3979, pp. 1230-1234, 2000.

* cited by examiner

MEDICAL VIEWING SYSTEM AND METHOD FOR ENHANCING STRUCTURES IN NOISY IMAGES

The invention relates to a viewing system for enhancing objects of interest represented in a sequence of noisy images including temporal enhancement and for displaying the sequence of enhanced images. The invention also relates to a computer executable image processing method to be used in said system and to a medical examination apparatus coupled to such a system. The invention finds for example its application in the medical field of cardiology, for enhancing thin objects of interest such as stents and vessel walls in angiograms.

A method for improving the visualization of low-contrast structures in medical images is already known from the publication entitled "Layer decomposition of coronary angiograms", by Robert A. Close et al, in Proceedings of the SPIE International Society for Optical Engineering, Vol. 3979, pages 1230-1234, 2000. This document describes an image processing method for improving the detection of low-contrast features such as stents in coronary x-ray images or angiograms. The basis for layer decomposition of coronary angiograms is the observation that although the anatomical motion is inherently three-dimensional and non-uniform, the motion of a small region can usually be approximated by a single rigid motion. In projection images, all layers contribute to the intensity of each pixel. Therefore, by decomposing an angiographic image sequence into moving layers, it is expected to separate the densitometric profile of the vessel from background structures that have different motion. Layer decomposition models the projections as a set of superposed layers moving with translation, rotation, and scaling. The layer motions are solved by using phase correlation techniques. The layer densities are solved by averaging along moving trajectories and subtracting new layer densities from previous layer estimates. The reconstructed vessel layer represents a motion-compensated temporal average of structures co-moving with the vessel. Subtraction of background layers from the original image sequence yields a tracked background-subtracted sequence that has no vessel-motion artifacts and almost no increase in noise, unlike standard background subtraction techniques. This method deeply relies on a localized block-matching (phase correlation) technique applied to every layer. This technique estimates separately the motion of the vessels and the motion of the background in order to subtract the motion of the background from the original image. Due to layer decomposition and block-matching, this method would present a calculation load actually too heavy for real time processing of an image sequence during an intervention phase. So, the proposed method may be preferably used in a post-intervention phase.

Instead, it is an object of the invention to propose a viewing system that has means to process images in real time. It is particularly an object of the invention to propose a medical viewing system that has means to process medical images in real time in order to be dynamically displayed during an intervention phase. The invention has especially for an object to provide means for enhancing low-contrast objects of interest, for minimizing noise and for fading the background in noisy images such as a sequence of medical fluoroscopic images. The invention has particularly for an object to provide means to process angiograms representing vessels and stents as objects of interest, which present a low contrast, which may be moving on the background, but not necessarily, and which have previously been detected and localized.

A stent is a surgical stainless steel coil that is placed in the artery in order to improve blood circulation in regions where a stenosis has appeared. When a narrowing called stenosis is identified in a coronary artery of a patient, a procedure called angioplasty may be prescribed to improve blood flow to the heart muscle by opening the blockage. In recent years, angioplasty increasingly employs a stent implantation technique. This stent implantation technique includes an operation of stent placement at the location of the detected stenosis in order to efficiently hold open the diseased vessel. The stent is wrapped tightly around a balloon attached to a monorail introduced by way of a catheter and a guide-wire. Once in place, the balloon is inflated in order to expand the coil. Once expanded, the stent, which can be considered as a permanent implant, acts like a scaffold keeping the artery wall open. The artery, the balloon, the stent, the monorail and the thin guide-wire are observed in noisy fluoroscopic images. These objects show low radiographic contrast that makes evaluation of the placement and expansion of said stents at an accurate location very difficult. Also, during the operation of stent implantation, the monorail, with the balloon and stent wrapped around it, is moving with respect to the artery, the artery is moving under the influence of the cardiac pulses, and said artery is seen on a background that is moving under the influence of the patient's breathing. These movements make the following of stent implantation under fluoroscopic imaging still more difficult to visualize. In particular, these movements make zooming inefficient because the object of interest may get out of the zoomed image frame. Clinical problems are associated with inadequate expansion of the stent, improper placement of the stent, and gap or overlap between several stents. Inadequately deployed stents can cause thrombosis. An other drawback of the bad images that were until now to the disposal of the clinician, is that it was necessary to use a contrast agent in a product introduced in the balloon for inflating said balloon in the operation of stent deployment. The use of the contrast agent prevents the clinician to distinguish the stent from the balloon and from the wall of the artery.

According to the invention, a viewing system and an image processing method are provided comprising means for acquiring a sequence of images, and for processing and displaying said images in real time. The system comprises initialization means applied to the original images for extracting and localizing an object of interest, which may be moving with respect to the referential of the image, the background being moving both with respect to said referential and with respect to the object. The initialization means then comprise registration means for registering the object of interest with respect to the referential of the image. According to the invention, this system further comprises processing means for automatically enhancing the object of interest, for minimizing the noise and for blurring or fading the background of the images. Said processing means include at least a means for carrying out a temporal integration technique performed on at least two images where the object of interest has been registered with respect to the referential of the images. Since after registration of the object, the background still moves with respect to the referential of the images, this temporal integration technique provides an enhancement of the object of interest, while minimizing the noise and blurring and fading the background.

Such a system is claimed in claim 1 and detailed embodiments are claimed in dependent claims. An image processing method to be used in the system, a program product to implement the steps of the method of the invention, and an examination apparatus associated to such a system are further claimed.

Embodiments of the invention are described hereafter in detail in reference to diagrammatic figures wherein.

The invention relates to a viewing system, and to a computer executable image processing method that is used in the viewing system, for enhancing objects of interest in a sequence of noisy images and for displaying the sequence of enhanced images. The viewing system and method have means to acquire, process and display the images in real time. The viewing system and the image processing method of the invention are described hereafter as a matter of example in an application to the medical field of cardiology. In said application, the objects of interest are organs such as arteries and tools such as balloons or stents. These objects are observed during a medical intervention called angioplasty, in a sequence of X-ray fluoroscopic images called angiograms. The system and method may be applied to any other objects of interest than stents and vessels in other images than angiograms. The objects of interest may be moving with respect to the image referential, but not necessarily, and the background may be moving with respect to the object or to the image referential.

Figure 2A:
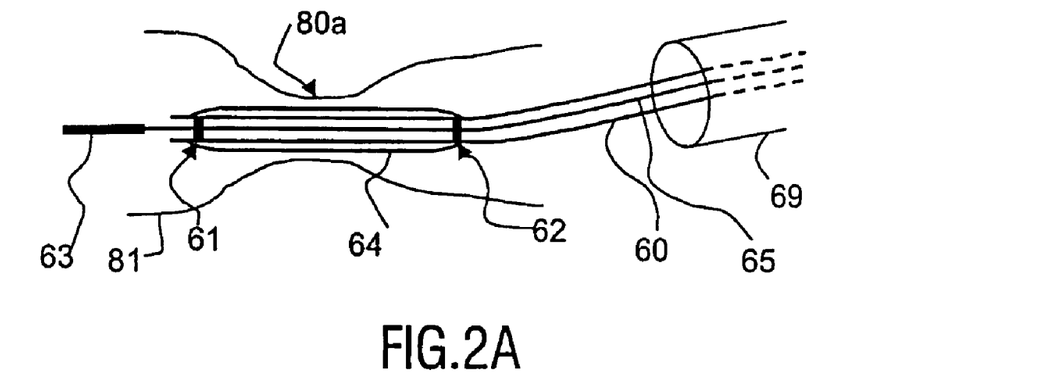
FIG. 2A to FIG. 2C illustrate intervention steps of angioplasty.
Figure 2B:
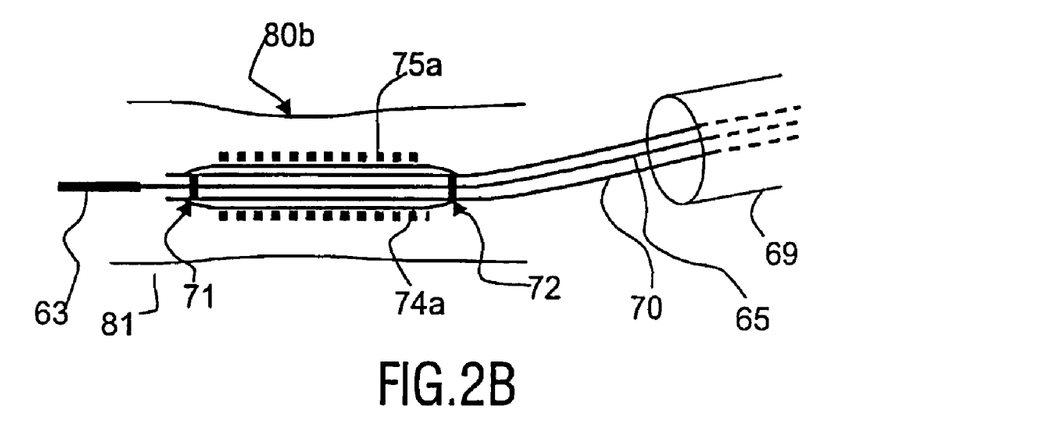
Figure 2C:
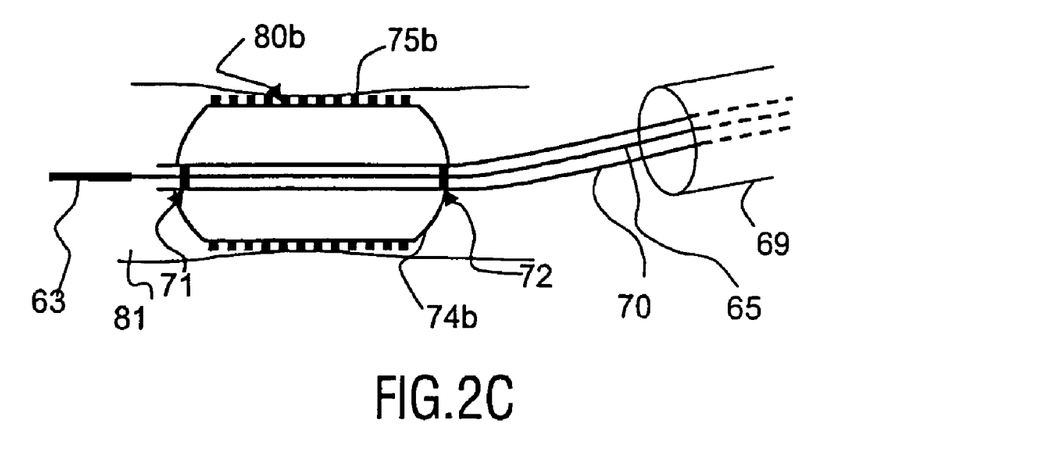

The embodiments described hereafter uniquely relate to an image processing system and an image processing method, and not to a diagnostic method. However, the images are acquired, in this example, as a sequence of images during a stent implantation, which is a medical intervention performed under fluoroscopy, and which usually comprises several steps for enlarging an artery at the location of a lesion called stenosis. Fluoroscopy is a low dose x-rays technique that yields very noisy and low contrasted images. Introducing a catheter in a patient artery in these conditions is a very delicate and dangerous operation. The embodiments of the invention do not permit the clinician to form a diagnosis. They only permit to provide the clinician, in real time, with greatly improved medical images with respect to the fluoroscopic images of the same objects that the clinician would have obtained without the system of the invention. In a preliminary step, the practitioner localizes the stenosis 80a in a patient's artery 81 as best as possible. A corresponding medical image is schematically illustrated by FIG. 2A. Then, the sequence of images to be processed is acquired as several sub-sequences during the steps of the medical intervention, comprising:

a) A sub-sequence of medical images, schematically illustrated by FIG. 2A, which displays the introduction in the artery 81 through a catheter 69 of a thin guide-wire 65 that extends beyond the extremity of the catheter 69, and passes through the small lumen 80a of the artery at the location of the stenosis; the introduction of a first monorail 60, which is guided by said guide-wire 65 having a first balloon 64 wrapped around its extremity, without stent; and the positioning of said first balloon 64 at the location of the stenosis 80a using the balloon-markers 61, 62.

b) A sub-sequence of medical images, schematically illustrated by FIG. 2A and FIG. 2B, which displays the inflation of this first balloon 64 for expanding the narrow lumen 80a of the artery 81 at the location of the stenosis to become the enlarged portion 80b of the artery; then, the removal of the first balloon 64 with the first monorail 60.

c) A sub-sequence of medical images, schematically illustrated by FIG. 2B, which displays the introduction of a second monorail 70 with a second balloon 74a wrapped around its extremity, again using the catheter 69 and the thin guide-wire 65, with a stent 75a wrapped around said second balloon 74a; and the positioning said second balloon with the stent at the location of the stenosis in the previously expanded lumen 80b of the artery 81 using the balloon-markers 71, 72. In a second way of performing the angioplasty, the clinician may skip steps a) and b) and directly introduce a unique balloon on a unique monorail, with the stent wrapped around it.

d) A sub-sequence of medical images, schematically illustrated by FIG. 2C, which displays the inflation of the second balloon 74a to become the inflated balloon 74b in order to expand the coil forming the stent 75a that becomes the expanded stent 75b embedded in the artery wall. In the second example, the unique balloon is directly expanded both to expand the artery and deploy the stent.

Then, considering the deployed stent 75b as a permanent implant, the sub-sequence of medical images, displays the removing of the second (or unique) balloon 74b, the second (or unique) monorail 70, the guide-wire 65 and catheter 69.

The medical intervention called angioplasty is difficult to carry out because the image sub-sequences or the image sequence are formed of badly contrasted medical images, where the guide-wire, balloon, stent and vessel walls are hardly distinguishable on a noisy background and are moreover submitted to motions. According to the invention, the viewing system comprises means not only for acquiring and displaying a sequence of images during the intervention, but for processing and displaying said images, which are greatly improved in real time during the intervention.

Figure 1A:
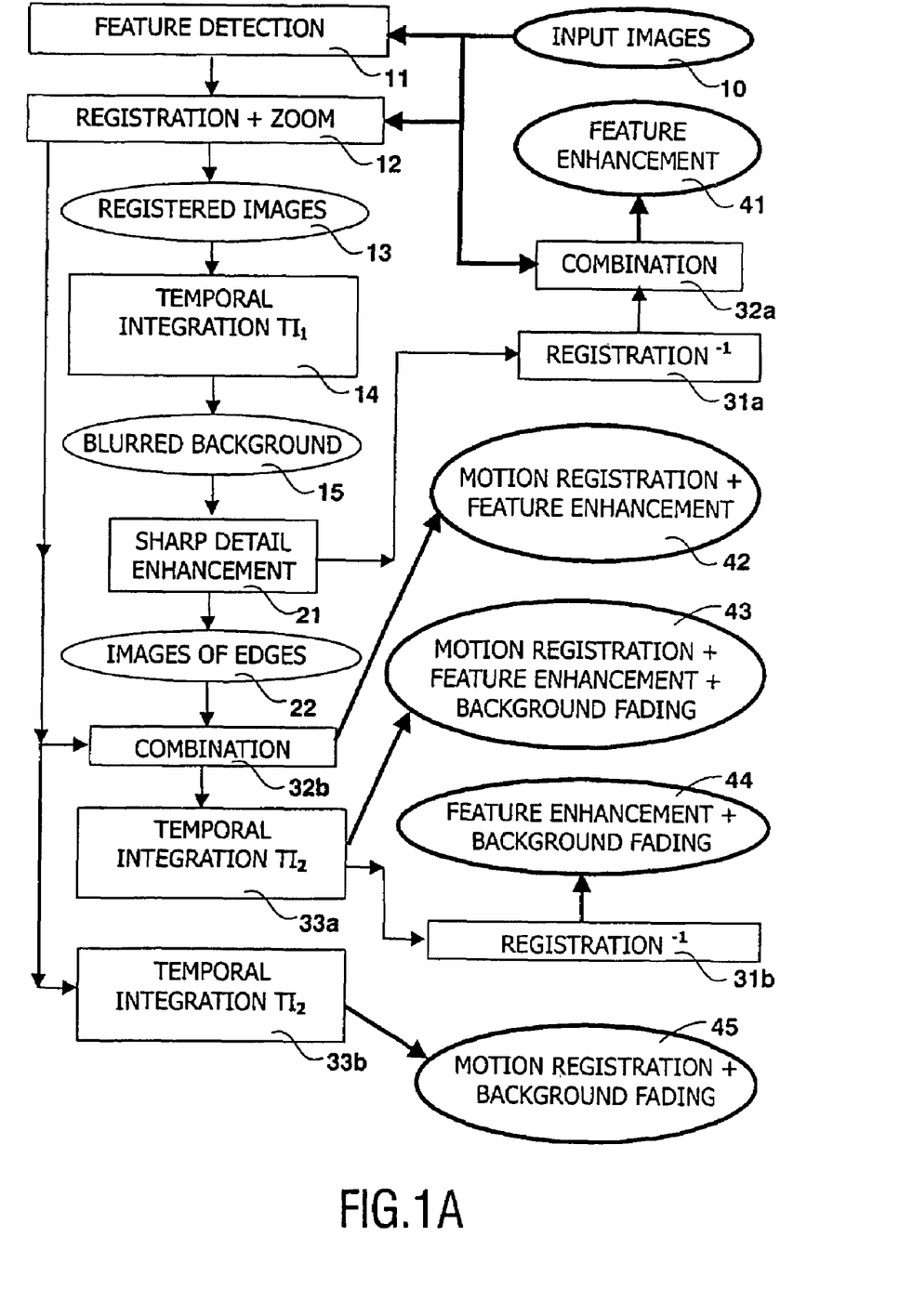
FIG. 1A and FIG. 1B are functional block diagrams of the system of the invention.

As illustrated by FIG. 1A, this system comprises initialization means applied to the original images for extracting and localizing the object of interest, which is usually moving with respect to the referential of the image, but not necessarily, the background being moving both with respect to said referential and with respect to the object. The extraction and localization means may localize the object directly. However, as the objects are hardly radio-opaque, they are preferably localized indirectly. According to the invention, the objects are localized by first localizing related markers. The initialization means then comprise registration means for registering the moving object of interest with respect to the image referential. This system further comprises processing means including at least a means for carrying out a temporal integration technique performed on at least two images. This technique is efficient to enhance the object of interest because said object has previously been registered with respect to the referential of the images. Since after registration of the object, the background still moves with respect to the referential of the images, the temporal integration technique provides sharp detail enhancement of the object of interest, while the details of the background are blurred. In other words, with the technique of the invention, the integration step integrates object pixels that correspond to same object pixels in successive images, so that their intensities are increased, while said integration step integrates background pixels that do not correspond to the same background pixels in the successive images, so that their intensities are decreased.

Hence, the important means of the invention is in fact a motion corrected temporal integration means, wherein the motion correction is applied to the object of interest and not to the background, while the temporal integration is applied both to the object of interest and to the background. In an example, the temporal integration means may comprise averaging means for averaging the pixel intensities, at each pixel location in the referential, on two or more images. In another example, the temporal integration means may comprise a recursive filter, which performs a weighted average of pixel intensity on succeeding images.

The enhancement of the object may be compared to the one obtained by having applied to the object an increase of the dose of x-rays during the formation of the sequence of images, since the intensities of the pixels of the object are increased due to the integration over several images. However, according to the invention, for efficiency of the temporal integration, this step is carried out on corresponding pixels, i.e. on a static object, which is obtained by the registration of the object performed in the preliminary steps. Now, regarding the background, the result obtained by temporal integration is completely different from the one obtained by increasing the dose of x-rays. Since according to the invention, after the registration step, the object is immobile with respect to the referential of the image, while the background still moves with respect to the object, it results that, by temporal integration, the background is blurred, smoothed and faded, the noise is minimized, while the details of the object are enhanced. Instead, by increasing the dose of x-rays, the details of the background would be enhanced in the same way as those of the object, which is not desirable. Increasing the dose of x-rays would also present the inconvenient to be dangerous for the patient and the clinician.

An advantageous integration means may comprise a determination of the resemblance of the object called object of interest detected in two successive images. In fact, if two different objects were detected, and integrated, their pixels would not correspond and the result of the integration step would be a blurred object. The determination of resemblance between an object of interest in a first image and the candidate to be called same object of interest in a succeeding image is performed using a criterion of similarity. This advantageous integration means comprises means to modulate an object pixel intensity in the current image in function of the result of the criterion. The system of the invention further comprises sharp detail enhancement means applied to the image after the first temporal integration. Then, the system may further comprise a second registering means that compensates for the remaining fine motion of the object with respect to the referential of the image and a second temporal integration phase to refine the object enhancement. The temporal integration technique applied to registered objects presents several essential advantages over using an increase of x-ray dose, without the inconvenient.

In the present example of application to cardiology, the user of the viewing system may be an actor of the medical intervention. In this case, he has the possibility to intervene during the image processing steps, for example while not moving the intervention tool or tools. First of all, the user might choose a region of interest in the images. Besides, the user has at his disposal control means 58, shown in FIG. 5, to activate and control the image processing means. These control means comprise starting means and stopping means for the user to start the image processing operation, to control the duration of the image processing operation and to end the image processing operation. In particular, the user may choose that the final processed images are compensated for the registration or not, depending on whether the motion of objects is of importance for the diagnosis or not.

Referring to FIG. 1A, the initialization means includes extracting means 11 that solves the problems of accurately localizing the object of interest in the sequence. The object of interest are preferably localized indirectly by localizing first specific features such as the guide-wire tip 63 or the balloon-markers 61, 62 or 71, 72. The marker 63, which is located at the extremity of the thin guide-wire 65, permits of determining the position of the guide-wire 65 with respect to the stenosed zone 80a of the artery 81; the balloon-markers 61, 62, which are located on the monorail 60 at a given position with respect to the balloon 64, permit of determining the position of the first balloon with respect to the stenosed zone before expanding the balloon in the lumen of the artery; the balloon-markers 71, 72, which are located on the monorail 70 at a given position with respect to the balloon 74a, permit of determining the position of the second balloon, with the stent 75a wrapped around it, before stent expansion and permits of finally checking the expanded stent 75b.

These specific features called tips or markers are far better contrasted than the stent or vessel walls. The extracting means 11 are appropriate to accurately extract said tips or markers from the original images 10. However, the clinician may choose to select the tips and markers manually or to improve manually the detection of their coordinates. These tips and markers have a specific easily recognizable shape, and are made of a material highly contrasted in the images. Hence they are easy to extract. It is to be noted that these specific features do not pertain to the badly contrasted stent or vessel walls, which are the objects that are actually finally of interest for the practitioner. The guide-wire tip 63 pertains neither to the artery walls 81 nor to the stent 75a, since it pertains to the guide-wire 65. Also, the balloon-markers 61, 62 or 71, 72 pertain neither to the vessel walls 81 nor to the stent 75a since they pertain to the monorail 60 or 70. The system processing means 11 permits of accurately deriving the location of the balloons 64, 74a, 74b, since the balloon-markers have a specific location with respect to the balloons. Also, the stents 75a, 75b are accurately localized, since the stents have a specific location with respect to the balloon-markers though said stents are not attached to said balloon-markers. Once the markers of an object of interest has been extracted, the registering means 12 registers the object of interest with respect to the referential of the images 10, preferably based on the marker location.

Figure 3:
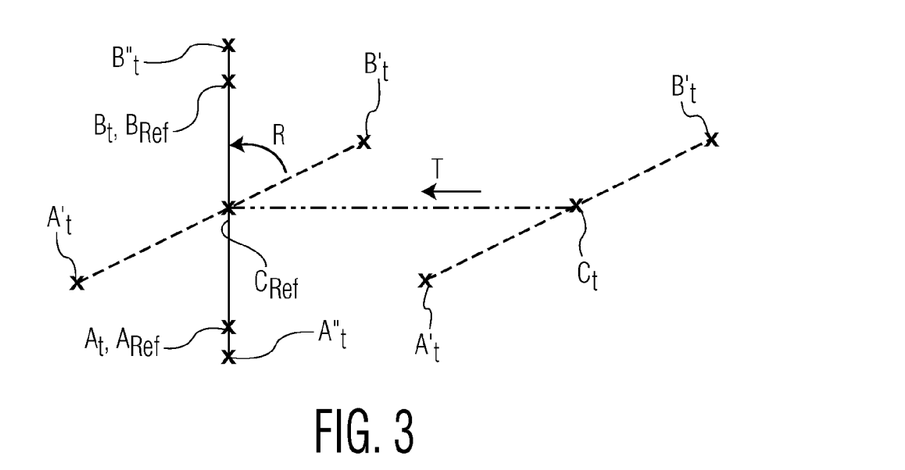
FIG. 3 illustrates a step of marker registration.

Referring to FIG. 3, for instance two markers $A_{Ref}$, $B_{Ref}$ have been detected in an image of the sequence, called image of reference, which may be the image at starting time. The markers $A_{Ref}$, $B_{Ref}$ may be selected by automatic means. Then, the registering means 12 of the system, using the marker location information $A_{Ref}$, $B_{Ref}$ in the reference image and corresponding extracted markers $A'_t$, $B'_t$ in a current image of the sequence 10, are operated for automatically registering the current image on the reference image. This operation is performed by matching the markers of the current image to the corresponding markers of the reference image, comprising possible geometrical operations including: A translation T to match a centroid $C_t$ of the segment $A'_tB'_t$ of the current image with a centroid $C_{Ref}$ of the segment $A_{Ref}B_{Ref}$ of the reference image; a rotation R to match the direction of the segment $A'_tB'_t$ of the current image with the direction of the segment $A_{Ref}B_{Ref}$ of the reference image, resulting in a segment $A''_tB''_t$; and a dilation $\Delta$ for matching the length of the resulting segment $A''_tB''_t$ with the length of the segment $A_{Ref}B_{Ref}$ of the reference image, resulting in the segment $A_tB_t$. Such operations of translation T, rotation R and dilation $\Delta$ are defined between the current image at a current instant t of the sequence and an image of reference, resulting in the registration of the whole sequence. This operation of registration is not necessarily performed on all the points of the images. Zones of interest comprising the markers may be delimited.

This operation of registration minimizes the effect of respective movements of the objects of interest, such as vessels, guide-wire, balloons and stent, with respect to a predetermined image referential. Preferably, two markers, or more, are used for better registration. The registration operation permits the user to easily perform a zooming Z on the object of interest, without the object evading from the frame of the image.

In the registered sequence 13, the pixels of the object of interest are now approximately static in the succeeding images. So, according to the invention, a registered object of interest is submitted to a first temporal integration means 14 over a first number of images, at least two images or more than two images; this first integration phase is denoted by $TI_1$. The first number of images for the first temporal integration is chosen according to a compromise to avoid blurring the object having residual motion and to cause the blurring of the background. As the background has not been registered with respect to the referential of the image, the details of the background are still moving with respect to the object. By integrating the approximately static pixels using the first temporal integration means, the intensity of each pixel is increased, while the details of the background are blurred. In an example, the registered images 13 are integrated by averaging means applied to the intensity of the pixels on the first number of images. By this operation, the details of objects, such as vessels, which are substantially in time concordance, are enhanced and the noise is minimized, while the details of the background, which are not in time concordance, are blurred. In another example, the temporal integration means is a recursive filter for combining the current original image at an instant t, where the intensities are denoted by X(t), to the image processed at a previous instant (t−1), where the intensities are denoted by Y(t−1), using a weighting coefficient β, according to a formula giving the intensities of the integrated current image:

$$Y(t)=Y(t-1)+\beta[X(t)-Y(t-1)] \quad [1]$$

Using this last technique, the images are more and more improved as the sequence proceeds. This operation yields an intermediate sequence 15 of registered enhanced images with a blurred background, further used for sharp detail enhancement.

Figure 1B:
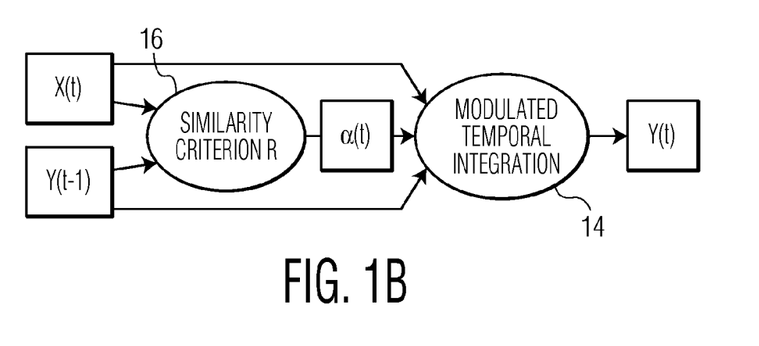

Creating a view in which the object of interest is registered and temporally integrated is a way to improve the visibility and reduce the noise. However, if the registration fails in one of the frames because of a wrong detection, the visibility of the object of interest in the temporal integrated view may decrease dramatically. This problem might arise anytime temporal integration is involved. Referring to FIG. 1B, according to the invention, the solution consists in checking the resemblance of the current not yet integrated (possibly registered) frame X(t) with the previously integrated view Y(t−1) in order to determine resemblance information, which resemblance information is then used to determine a modulation coefficient α. Said modulation coefficient α is further used in order to modulate the importance of the current frame in the registered view Y(t), during temporal integration. The resemblance information between X(t) and Y(t−1) is measured by a similarity criterion 16, denoted by R. This similarity criterion R may be a correlation or a normalized correlation. If the criterion R gives a low result, the weight of the current image X(t) in Y(t) will be low.

The temporal integration 14 may be recursive, hence the weight is α(t) that depends on time. In that case:

$$Y(t)=\alpha(t).Y(t-1)+(1-\alpha(t)).X(t) \quad [2]$$

with α(t)=f(R(t)).

The previously temporally processed sequence of images with blurred background 15 is submitted to the enhancing means 21, which may be a spatial filter such as an edge filter. This edge filter extracts the sharp details of the object of interest and yields images of edges 22. The user may choose to restore the motion of the objects before displaying the sequence of images. In this case, the sharp detail enhancement means 21 yields the images of edges 22 to inverse registration means denoted by registration means power minus one 31a, which causes motion restitution. The images with restored motion are combined by combination means 32a to the input images 10 to yield a first interesting image sequence 41 of original objects with enhanced edges and with their original motion and original background, to be displayed to the user on the display means 54 of the viewing system shown on FIG. 5. The images of edges 22, yielded by said sharp detail enhancement means 21, may alternately be entered together with the registered images 13, yielded by the registration means 12, in a combination means 32b for enhancing the edges of the objects in the registered images 13. This combination means 32b yields a second interesting image sequence 42 of registered objects with enhanced edges on the original background, to be displayed on the display means 54.

The registered images 42 with enhanced sharp details, issued by the combination means 32b, are further submitted to a second registration means to eliminate residual motion of the object, because in fact, after the first registration performed by means 12, the object of interest may still be submitted to small residual motion with respect to the image referential, for the reason that the markers are the actually registered features and that said markers are not attached to the object of interest. Then, the images are submitted to a second temporal integration means 33a for causing background fading. The second temporal integration technique may be the same as the first one. The second integration phase may be performed on a second number of images, preferably greater than or equal to the first number used in the first integration means 14, and is denoted by $TI_2$. The second temporal integration phase TI2 has for advantage to provide a third interesting sequence of images 43 with motion registration, sharp feature enhancement of the objects of interest and background fading, to be displayed on the display means 54. The previously enhanced objects are again enhanced while the moving details of the background are faded.

Now that the objects are registered in the images and that the details are enhanced, the user can easily zoom on details of an object with the advantage that the object does not evade from the frame of the image. This zooming possibility is particularly important in the operation of balloon and stent positioning.

It has been noted above that, thanks to the image processing means of the invention, it is no more necessary for the practitioner to introduce a contrast agent in the balloon for inflating the balloon, since the balloon is better visualized together with the stent without contrast agent. This property is also particularly useful when it is necessary to visualize a sequence of images of an intervention comprising the introduction and positioning of two stents side by side in the same artery. The first stent is clearly visualized after its deployment. Then the second stent is visualized and located by the detection of its markers. These objects are further registered and enhanced, which permits the practitioner of visualizing the second balloon during inflation and the stent during deployment, in dynamic instead of in static as was the case when contrast agent was necessary to localize the balloon.

Normally, the practitioner may position the two stents very near from one another when necessary because their visualization is excellent.

The user may choose to examine the sequence of images with the original movements of the objects. In this case, the second temporal integration means 33a yields the images 42 to inverse registration means 31b, which causes motion restitution and yields a fourth interesting image sequence 44 of objects with enhanced edges and with their original motion and faded background, to be displayed on the display means 54 of the viewing system shown on FIG. 5. Now, the user may choose to simply observe the registered object on a faded background. In that case, the images yielded by the registration means 12, possibly zoomed, are provided to the second temporal integration means 33b, denoted TI2, and further issued to the display means 54. It is to be noted that this simple operation is efficient enough because the residual motion of the object of interest is generally very small and because the background is generally rapidly fading after integration over a small number of images. This provides a fifth interesting image sequence 45 of registered objects with faded background, to be displayed on the display means 54 of the viewing system shown on FIG. 5.

A computer executable image processing method to be used in a system as above described has steps of processing a sequence of digital images during the medical intervention, comprising extracting at least a marker that pertains neither to the tool nor to the body organ, determining the marker location information in the images of the sequence, deriving the object location information from the marker location information, and processing the images to improve the visibility of the tool and/or of the organ. The method permits of displaying the images during the medical intervention for the user to position the tool in the organ at a specific location using these enhanced images. In the application to angioplasty, the result of these image processing operations for example permits of checking the proper expansion of the lumen of the artery and permits of checking the proper expansion of the stent.

Figure 4A:
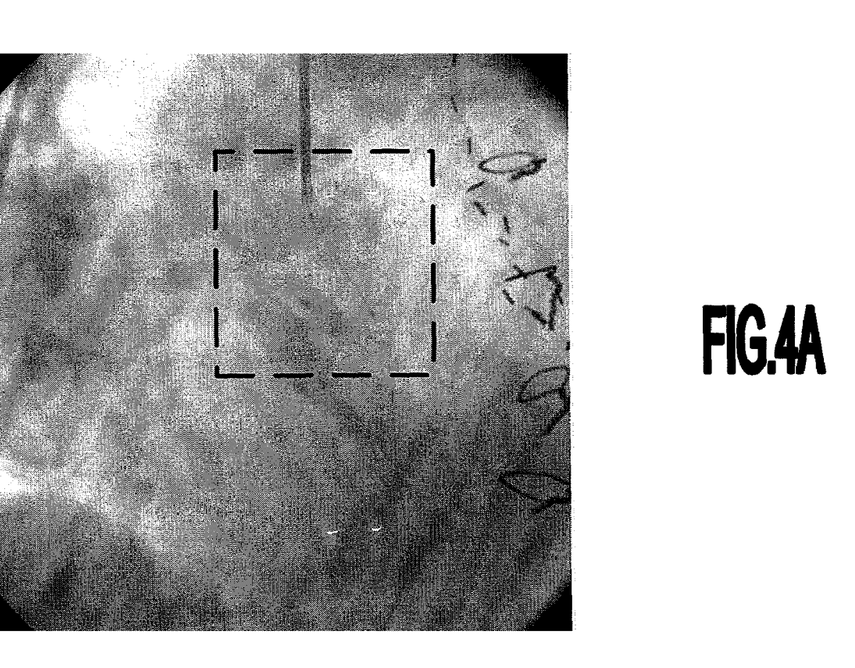
FIG. 4A shows an original angiogram and FIG. 4B shows a processed image with zooming on an enhanced object of interest and with background fading.
Figure 4B:
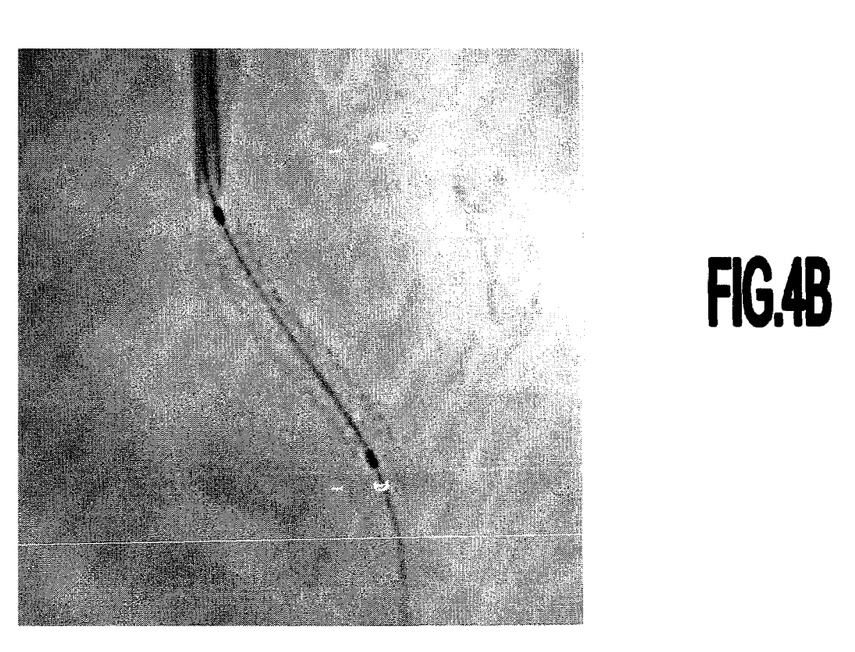

FIG. 4A shows an original image of a medical sequence representing a catheter, a guide wire, a balloon with balloon-markers (as two small dark points) and an artery on a background of other organs. The visualization of the objects of interest (balloon and artery) is very difficult. Even the balloon-markers are hardly visible. The doted line represents the frame of the zoomed image of FIG. 4B. In FIG. 4B, the image has been processed according to the invention: hence the objects of interest are enhanced and the background is completely faded.

The imaging system means and imaging method of the present invention permit of improving the images of the sub-sequence that are acquired as described above in step c), in reference to FIG. 2C, in such a way that the medical intervention steps may be simplified. In fact, for deploying the balloon in step c), starting from the shape 74a to yield the shape 74b, the practitioner must introduce an inflation product into the balloon. Without the viewing system of the invention, the practitioner generally uses an inflation product that comprises a large amount of a contrast agent in order to be able to visualize the balloon. This contrast agent has for an effect to render the balloon and stent as a sole dark object in the images of the sub-sequence. When using such a contrast agent, the balloon and stent are not distinguishable from one another during the balloon inflation and stent deployment. The practitioner must wait until the removing of the darkened balloon for at last having a view of the deployed stent alone, and it is only a static view. Instead, the imaging system means and imaging method of the present invention permit of avoiding the use of contrast agent in the inflation product, or to use a substantially small amount of such a contrast agent in the product during the operation of balloon inflation and stent deployment. Since the balloon now remains transparent, said imaging system means and imaging method of the present invention permit of dynamically following the inflation of the balloon and stent deployment in all the images of the sequence. Said imaging system means and imaging method of the present invention permit of dynamically visualizing the balloon and the stent independently during the operations of inflation of the balloon and stent deployment. This results are due to the fact that the object of interest are registered in the images, zoomed and enhanced in such an improved manner that it is no more necessary to use the contrast gent to permit the practitioner of localizing and visualizing them. Of course, these results are only obtained thanks to the sophisticated means of the invention.

Figure 5:
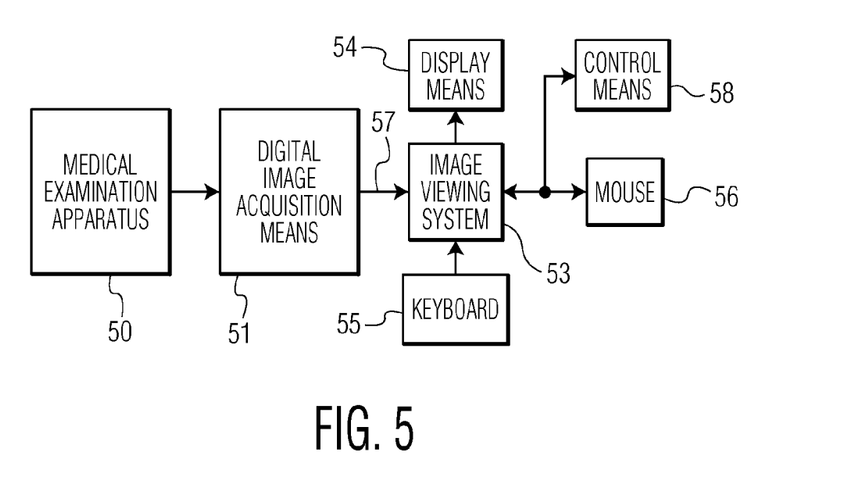
FIG. 5 is a functional block diagram of a medical examination apparatus.

FIG. 5 shows a diagram of a medical examination apparatus 50. The apparatus has means 51 for acquiring digital image data of a sequence of images, and is coupled to a medical viewing system 53 as described above, for processing these data according to the processing method cited above. The medical viewing system is generally used in the intervention room or near the intervention room for processing real time images. Should steps of the present method be applied on stored medical images, for example for estimating medical parameters, the system for processing the data of the stored images would be called medical viewing station. The medical examination apparatus provides the image data by connection 57 to the system 53. The system provides processed image data to display and/or storage means. The display means 54 may be a screen. The storage means may be a memory MEM of the system 53. Said storage means may be alternately external storage means. This image viewing system 53 may comprise a suitably programmed computer, or a special purpose processor having circuit means such as LUTs, Memories, Filters, Logic Operators, that are arranged to perform the functions of the method steps according to the invention. The system 53 may also comprise a keyboard 55 and a mouse 56. Icones may be provided on the screen to be activated by mouse-clicks, or special pushbuttons may be provided on the system, to constitute control means 58 for the user to start, to control the duration or to stop the processing means of the system at chosen phases.

The invention claimed is:

1. A viewing system for enhancing objects of interest represented on a moving background in a sequence of noisy images and for displaying the sequence of enhanced images, including acquisition means for acquiring the sequence of images and processing means for processing the images comprising extracting means for extracting features related to an object of interest on a background in images of the sequence having an image referential, said processing means further comprising: a first registering means, yielding registered images, for registering the features related to the object of interest with respect to the image referential, while not registering the background; a first temporal integration means for integrating both the object of interest and the background over at least two registered images of the sequence; a second registering means and a second temporal integrating means for integrating the registered object of interest with enhanced edges and the moving background over at least two images of the sequence, yielding images of the registered object of interest with enhanced edges and faded background to the display means and display means for displaying the processed images of the enhanced registered object of interest on faded background.

2. The system of claim 1, having control means for a user to activate the processing means, control duration of the processing means, or stop the processing means at a selected stage in the sequence of images.

3. The system of one of claim 1, wherein the processing means further comprises: similarity detection means for determining resemblance information in one or more representations of a registered object of interest in succeeding images; and weighing means using said resemblance information for modulating the intensities of the pixels of said object of interest over the images of the sequence, during temporal integration by the temporal integration means.

4. The system of one of claim 1, wherein the processing means further comprises: enhancement means for spatially enhancing sharp details in the images issued from the temporal integration means (14), yielding images of edges of the object of interest; combination means for combining the registered images yielded by the first and second registration means and the images of edges yielded by a filtering means, yielding images of the registered object of interest with enhanced edges to the display means.

5. The system of claim 4, further comprising inverse registration means to restitute the motion of the object of interest, yielding to the display means images of the object of interest moving with respect to the image referential.

6. The system of claim 5, wherein the inverse registration means to restitute the motion of the object of interest is applied to the images of the registered object of interest with enhanced edges and faded background yielded by the second temporal integration means, yielding to the display means images of the object of interest having enhanced edges, moving with respect to the image referential, and with faded background.

7. The system of claim 5, wherein the inverse registration means is applied to the images of enhanced edges yielded by the spatial filter, to restitute the original motion to said enhanced edges, the system further comprising: combination means for combining the original images and the images of edges with original motion, yielding to the display means images of the original object of interest with enhanced edges.

8. The system of claim 1, wherein the first registration means further comprises zooming means for zooming a registered object of interest.

9. The viewing system of claim 1, for dynamically displaying a sequence of medical images of a medical intervention that comprises moving and/or positioning a tool called balloon, in an artery, said balloon and artery being considered as objects of interest, and said balloon being carried by a support called monorail, to which at least two localizing features called balloon-markers are attached and located in correspondence with the extremities of the balloon, wherein: the extracting means extracts the balloon-markers considered as features related to the objects of interest, which balloon-markers pertain neither to the balloon nor to the artery; the registering means registers the balloon-markers and the related balloon and artery in the images; the processing means, comprising at least temporal integration means and sharp detail enhancement means, yield images of enhanced balloon and artery; and: the display means dynamically displays the images during the medical intervention for the user to visualized images of the balloon during its positioning in the artery, at a specific location of a portion of the artery, with respect to the balloon-marker extracted location.

10. The system of claim 1, for dynamically displaying a sequence of images of an intervention, which comprises moving and/or positioning a tool called stent wrapped around a balloon in an artery, said balloon, stent and artery being considered as objects of interest, which stent and balloon are carried by the monorail to which at least two localizing features called balloon-markers are attached and located in correspondence with the extremities of the balloon, wherein: the extracting means extracts the balloon-markers considered as features related to the objects of interest, which balloon-markers pertain neither to the balloon nor to the stent and nor to the artery; the registering means registers the balloon-markers and the related balloon, stent and artery in the images; the processing means, comprising at least temporal integration means and sharp detail enhancement means, yield images of enhanced balloon, stent and artery; and: the display means dynamically displays the images during the medical intervention for the user to visualize images of the balloon during its positioning in the artery, at a specific location of a portion of the artery, with respect to the balloon-marker extracted location; the display means dynamically displays the images during the medical intervention for the user to visualize images of the balloon with the stent during their positioning in the artery, at a specific location of a portion of the artery, with respect to the balloon-marker extracted location, and for the user to further visualize images of the stent deployment during a stage of balloon inflation with an inflation product without or with substantially few contrast agent.

11. The system of claim 9, comprising: selecting means for selecting an image of the sequence called reference image, and at least a marker called reference marker in the reference image related to an object of interest; and system wherein: the first registering means uses the marker location information in the reference image and in a current image of the sequence, for registering the marker and the related object of interest of the current image by matching the marker of the current image to the reference marker of the reference image.

12. A computer executable image processing method, for enhancing objects of interest represented on a moving background in a sequence of noisy images, for displaying the sequence of enhanced images, for acquiring the sequence of images, for processing the images, and for extracting features related to an object of interest on a background in images of the sequence having an image referential, the method comprising acts of:
  registering the features related to the object of interest with respect to the image referential, while not registering the background, yielding registered images;
  temporally integrating both the object of interest and the background over at least two registered images of the sequence;
  registering and temporally integrating the registered object of interest with enhanced edges and the moving background over at least two images of the sequence, yielding processed images of the registered object of interest with enhanced edges and faded background; and
  displaying the processed images of the enhanced registered object of interest on faded background.

13. A computer readable medium having processor-executable instructions thereon which, when executed by a processor, direct the processor to carry out an image processing method for enhancing objects of interest represented on a moving background in a sequence of noisy images, for displaying the sequence of enhanced images, for acquiring the sequence of images, for processing the images, and for extracting features related to an abject of interest on a background in images of the sequence having an image referential, the processor-executable instructions comprising:
  a portion for registering the features related to the object of interest with respect to the image referential, while not registering the background, yielding registered images;

a portion for temporally integrating both the object of interest and the background over at least two registered images of the sequence;

a portion for registering and temporally integrating the registered object of interest with enhanced edges and the moving background over at least two images of the sequence, yielding processed images of the registered object of interest with enhanced edges and faded background; and a portion for providing the processed images of the enhanced registered object of interest on faded background to a display device for displaying.

14. A medical examination imaging apparatus having means for acquiring a sequence of medical images and having a viewing system for processing and for displaying said sequence of images according to claim 1.

* * * * *